(12) United States Patent
Kwoh et al.

(10) Patent No.: US 7,074,407 B1
(45) Date of Patent: Jul. 11, 2006

(54) METHOD FOR INCREASING HDL CHOLESTEROL LEVEL

(75) Inventors: Deborah J Kwoh, Carlsbad, CA (US); Steven W Brostoff, Carlsbad, CA (US); Dennis J Carlo, Rancho Santa Fe, CA (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 09/523,033

(22) Filed: Mar. 10, 2000

Related U.S. Application Data

(63) Continuation of application No. 08/482,454, filed on Jun. 6, 1995.

(51) Int. Cl.
*A61K 39/00* (2006.01)
*A61K 39/385* (2006.01)

(52) U.S. Cl. .............................. 424/184.1; 424/197.11
(58) Field of Classification Search .............. 424/184.1, 424/197.11
See application file for complete search history.

(56) References Cited

U.S. PATENT DOCUMENTS

| | | | |
|---|---|---|---|
| 5,242,687 A | 9/1993 | Tykocinskli et al. | |
| 5,264,341 A * | 11/1993 | Maciak et al. .............. | 435/7.21 |
| 5,279,540 A | 1/1994 | Davidson | |
| 5,338,829 A | 8/1994 | Weiner et al. | |
| 5,705,388 A | 1/1998 | Couture et al. | |
| 5,843,446 A | 12/1998 | Ladd et al. | |
| 5,994,310 A | 11/1999 | Buettner et al. | |
| 6,143,305 A | 11/2000 | Stevens | |
| 6,284,533 B1 | 9/2001 | Thomas | |
| 6,410,022 B1 | 6/2002 | Rittershaus | |

FOREIGN PATENT DOCUMENTS

| | | |
|---|---|---|
| EP | 0343460 A2 | 11/1989 |
| EP | 0752886 B1 | 1/1998 |
| WO | WO 90/15627 | 12/1990 |
| WO | WO 92/10203 | 6/1992 |
| WO | WO 93/11782 | 6/1993 |
| WO | WO 93/23076 | 11/1993 |
| WO | WO 94/24567 | 10/1994 |
| WO | WO 94/25060 | 11/1994 |
| WO | WO 95/04755 | 2/1995 |
| WO | WO 95/05849 | 3/1995 |
| WO | WO 96/15141 | 5/1996 |
| WO | WO 96/34888 | 11/1996 |
| WO | WO 96/39168 | 12/1996 |
| WO | WO 97/41227 | 11/1997 |

OTHER PUBLICATIONS

Abbey and Calvert, "Effects of Blocking Plasma Lipid Transfer Protein Activity in the Rabbit," *Biochimica et Biophysica Acta*. 1003:20-29 (1989).

Barter et al., *Biochimica et Biophysica Acta*, 531:233-236 (1978).
Bravo et al., *J. Biochem.* 116:1088-1095 (1994).
Evans et al., "Inhibition of Cholesteryl Ester Transfer Protein in Normocholesterolemic and Hypercholesterolemic Hamsters: Effects on HDL Supspecies, Quantity, and Apolipoprotein Distribution," *J. Lipid Res.* 35:1634-1645 (1994).
Gaur et al., "Bypass by an Alternate 'Carrier' of Acquired Autoimmunity From Pathogenic to Preventive," *International Immunology* 2:151-155 (1990).
Lasunción et al., "High-Density Lipoprotein Subpopulations As Substrates For The Transfer of Cholesteryl Esters To Very-Low-Density Lipoproteins," *Biochem. J.* 270:441-449 (1990).
Leff D., "Anti-Atherosclerosis Vaccine Aims to Turn Autoimmunity From Pathogenic to Preventive," *BioWorld Today* 6(95):1&3 (1995).
Leff, *Bioworld Today* 6(95):1-4 (1995).
Smith et al., "Preparation of an Anti-Peptide Antiserum Specific For Cholesteryl Ester Transfer Protein (CETP)," *Med. Sci. Res.* 21:911-912 (1993).
Swenson et al., "Mechanism of Cholesteryl Ester Transfer Protein Inhibition by a Neutralizing Monoclonal Antibody and Mapping of the Monoclonal Antibody Epitope," *J. Biol. Chem.* 264:14318-14326 (1989).
Tall A.R., "Plasma Cholesteryl Ester Transfer Protein and High-Density Lipoproteins: New Insights From Molecular Genetic Studies," *J. Internal Medicine* 237:5-12 (1995).
Tall et al, *J. Lipid Res.*, 27:361-367.
Talwar et al., "A Vaccine That Prevents Pregnancy in Women," *Proc. Natl. Acad. Sci. USA* 91:8532-8536 (1994).
Wang et al., "Identification of a Sequence Within the C-terminal 26 Amino Acids of Cholesteryl Ester Transfer Protein Responsible for Binding a Neutralizing Monoclonal Antibody and Necesary for Neutral Lipid Transfer Activity," *J. Biol. Chem.* 267:17487-17490 (1992).
Warnick et al., "A Comprehensive Evaluation of the Heparin-Maganese Precipitation Procedure For Estimating High Density Lipoprotein Cholesterol," *J. Lipid Res.* 19:65-76 (1978).

(Continued)

*Primary Examiner*—Mark Navarro
(74) *Attorney, Agent, or Firm*—Leon R. Yankwich; David G. O'Brien; Yankwich & Associates, P.C.

(57) ABSTRACT

The present invention provides a method for increasing HDL cholesterol in a mammal by stimulating an immune response that inhibits the function of CETP. Such an immune response can be induced by immunizing with CETP or fragments of CETP (together termed "CETP Peptides") which contain an epitope capable of stimulating such a response. The peptides can be conjugated to a carrier, such as KLH or ovalbumin, in order to increase immunogenicity. Adjuvants can also be administered.

8 Claims, No Drawings

OTHER PUBLICATIONS

Whitlock et al., "Monoclonal Antibody Inhibition of Cholesteryl Ester Transfer Protein Activity in the Rabbit," *J. Clin. Invest.* 84:129-137 (1989).
Yen et al., "Inhibition of Cholesteryl Ester Transfer Protein Activity by Monoclonal," *J. Clinical Investigation* 83(6):2018-2024.
Albers et al., *Arteriosclerosis*, 4: 49-58 (1984).
Alberts et al., *Molecular Biology of the Cell*, $2^{nd}$ ed., (Garland Publishing, Inc., NewYork, NY., 1989) pp. 1006-1007.
Alexander et al., *Immunity*, 1: 751-761 (1994).
Bahou et al., *J. Cin. Invest.*, 84: 56-61 (1989).
Barter et al., *J. Lipid Res.*, 21: 238-249 (1980).
Bevilacqua et al., *J. Clin. Invest.*, 91: 379-387 (1993).
Bisgaier et al., *J. Lipid Res.*, 34: 1625-1634 (1993).
Bisgaier et al., *J. Lipid Res.*, 32: 21-23 (1991).
Breslow et al., *Proc. Natl. Acad. Sci. USA*, 90: 8314-8318 (1993).
Brown et al., *Nature*, 342: 448-451 (1989).
Burtis and Ashwood, eds., *Tietz Textbook of Clinical Chemistry, second edition* (W.B. Saunders Co., Philadelphia, 1994), Table 41-20.
Carlsson et al., *Biochem. J.*, 173: 723-737 (1978).
Casali et al., *Science*, 234: 476-479 (1986).
Castelli et al., *J. Am. Med. Assoc.*, 256: 2835-2838 (1986).
Drayna et al., *Nature*, 327: 632-634 (1987).
Eldridge et al., in *Immunobiology of Proteins and Peptides V: Vaccines; Mechanisms, Design, and Applications*, Atassi, M.Z., ed. (Plenum Press, New York, 1989), pp. 191-202.
Engelhard, Victor H., *Sci. Am.*, 54-60 (1994).
Etlinger et al., *Science*, 249: 423-425 (1990).
Etlinger, H., *Immunol. Today*, 13: 52-55 (1992).
Fielding et al., *J. Lipid Res.*, 36: 211-228 (1995).
Gavish et al., *J. Lipid Res.*, 28: 257-267 (1987).
Gaynor et al., *Atherosclerosis*, 110: 101-109 (1994).
Gordon et al., *N. Engl. J. Med.*, 321: 1311-1316 (1989).
Green et al., *Cell*, 28: 477-487 (1982).
Greenspan & Baxter, eds., *Basic and Clinical Endocrinology $4^{th}$ ed.*, (Appleton & Lange, Inc., Norwalk, Connecticut, 1994), p. 432 (referring to the specifics of Gonadotropin-Releasing hormone).
Guyard-Dangremont et al., *Chim. Clin. Acta*, 231: 147-160 (1994).
Ha et al., *Biochim. Biophys. Acta*, 833: 203-211 (1985).
Ha et al., *Comp. Biochem. Physiol.*, 83B: 463-466 (1986).
Havel et al., "Introduction: Structure and metabolism of plasma lipoproteins", In *The Metabolic Basis of Inherited Disease, 6th ed.*, pp. 1129-1138 (Scriver, et al., eds.) (McGraw-Hill, Inc., New York, 1989).
Hayek et al., *J. Clin. Invest.*, 90: 505-510 (1992).
Hayek et al., *J. Clin. Invest.*, 91: 1665-1671 (1993).
Hesler et al., *J. Biol. Chem.*, 263: 5020-5023 (1988).
Hesler et al., *J. Biol. Chem.*, 262: 2275-2282 (1987).
Hopp and Woods, *Proc. Natl. Acad. Sci. USA*, 78: 3824-3828 (1981).
Ikewaki, et al., *J. Clin. Invest.*, 96: 1573-1581 (1995).
Inazu et al., *N. Engl. J. Med.*, 323: 1234-1238 (1990).
Jameson and Wolf, *CABIOS*, 4: 181-185 (1988).
Jarnagin et al., *Proc. Natl. Acad. Sci. USA*, 84: 1854-1857 (1987).
Jiang et al., *J. Biol. Chem.*, 266: 4631-4639 (1991).
Jiang et al., *J. Biol. Chem.*, 268: 27406-27412 (1993).
Jorieux et al., *Brit. J. of Haematology*, 87: 113-118 (1994).
Kligfield et al., *Am. Heart J.*, 112(3): 589-597 (1986).
Korn et al., *J. Mol. Biol.*, 65: 525-529 (1972).
Kushwaha et al., *J. Lipid Res.*, 34: 1285-1297 (1993).
Madden et al., *Ann. Rev. Immunol.*, 13: 587-622 (1995).
Mader, S.S., In *Human Biology, 4th ed.*, pp. 83, 102 (Wm. C. Brown Publishers, Dubuque, Iowa, 1995).
Marguerite et al., *Mol. Immunol.*, 29: 793-800 (1992).
Marotti et al., *Nature*, 364: 73-75 (1993).
Mathews, C.K. and van Holde, K.E., *Biochemistry*, pp. 574-576, 626-630 (The Benjamin/Cummings Publishing Co., Redwood City, California, 1990).
Means and Feeney, *Bioconjugate Chem.*, 1: 2-12 (1990).
Mezdour et al., *Clin. Chem.* 40/4: 593-597 (1994).
Michel et al., *Am. Heart J.* 117(3): 756-767 (1989).
Miller et al., *Am. Heart J.*, 113: 589-597 (1987).
Nagashima et al., *J. Lipid Res.*, 29: 1643-1649 (1988).
Palker et al., *Proc. Natl. Acad. Sci. USA*, 84: 2479-2483 (1987).
Panina-Bordignon et al., *Eur. J. Immunol.*, 19: 2237-2242 (1989).
Pruitt et al., *J. Surg. Res.*, 50: 350-355 (1991).
Pruitt et al., *Transplantation*, 52: 868-873 (1991).
Quig et al., *Ann. Rev. Nutr.*, 10: 169-193 (1990).
Quinet et al., *J. Clin. Invest.*, 85: 357-363 (1990).
Raju et al., *Eur. J. Immunol.*, 25: 3207-3214 (1995).
Rosen et al., *J. Immunol. Methods*,172: 135-137 (1994).
Rye et al., *J. Biol. Chem.*, 270: 189-196 (1995).
Sad et al., *Immunol.*, 76: 599-603 (1992).
Stern et al., *Nature*, 368: 215-221 (1994).
Suckling, Keith E., *Bio/Technology*, 12: 1379-1380 (1994).
Swenson et al., *J. Biol. Chem.*, 263: 5150-5157 (1988).
Tall, A.R., *J. Clin. Invest.*, 89: 379-384 (1990).
Tall, A.R., *J. Lipid Res.*, 34: 1255-1274 (1993).
Tam, J.P., *Proc. Natl. Acad. Sci. USA*, 85: 5409-5413 (1988).
Tao et al., *Nature*, 362: 755-758 (1993).
Tato et al., *Arterioscler. Thromb. Vascular Biol.*, 15: 112-120 (1995).
*The Merck Manual of Diagnosis and Therapy, $16^{th}$ ed.*, (Merck & Company Inc., Rahway, New Jersey, 1992), pp. 22-23 (referring to infection prevention), pp. 114-115 (referring to bacterial diseases), pp. 1944-1947 (referring to health management of neonates, infants, and children).
Travis, *Science*, 262: 1974-1975 (1993).
Wang et al., *Science*, 254: 285-288 (1991).
Wang et al., *J. Biol. Chem.*, 268: 1955-1959 (1993).
Wang et al., *J. Biol. Chem.*, 270: 612-618 (1995).
Ware et al., *P.N.A.S. USA*, 85: 3165-3169 (1988).
Watanabe et al., *Proc. Natl. Acad. Sci. USA*, 89: 5103-5107 (1992).
Watson et al., *Molecular Biology of the Gene, $4^{th}$ ed.*, (The Benjamin/Cummings Publishing Company, Inc., Menlo Park, California, 1987), p. 836.
Wedrychowski et al., *Biotechnology*, 11(4): 486-489 (1993).
Weisman et al., *Science*, 249: 146-151 (1990).
Yeh et al., *J. Immunol.*, 146: 250-256 (1991).
Zannis et al., "Genetic mutations affecting human lipoproteins, their receptors, and their enzymes", In *Advances in Human Genetics*, vol. 21, pp. 145-319 (Plenum Press, New York, 1993).
Zegers et al., *Eur. J. Immunol.*, 23: 630-634 (1993).

\* cited by examiner

METHOD FOR INCREASING HDL CHOLESTEROL LEVEL

This application is a CON of Ser. No. 08/482,454, filed on Jun. 6, 1995.

This invention relates generally to the field of immunotherapy and, more specifically, to methods of stimulating an immune response to cholesteryl ester transfer protein (CETP).

BACKGROUND OF THE INVENTION

Blood cholesterol levels have long been thought to correlate directly with risk of atherosclerotic cardiac disease, the leading cause of heart attacks. More recently, it has been appreciated that blood cholesterol is actually composed of two primary forms: the high density lipoproteins (HDL) and low density lipoproteins (LDL). Rather than being associated with the disease risk, high HDL levels are apparently inversely predictive. In fact, studies have now indicated that HDL has a direct action in protecting against atherosclerosis and may even promote atherosclerosis plaque regression.

Numerous factors are involved in regulating the level of cholesterol in the body. Cholesteryl ester transfer protein (CETP) is an enzyme responsible for transporting cholesterol esters (CE) from HDL to very low density lipoproteins (VLDL) and LDL. VLDL's are eventually converted into LDL. CETP accelerates specifically the exchange of lipid components between pro- and anti-atherogenic lipo protein tractions. In particular, there is a strong inverse correlation between the levels of CETP in the plasma and the levels of HDL cholesterol. CETP activity levels are elevated in individuals suffering from dietary or genetic hypercholesterolemia. Increased levels of CETP activity result in lowered levels of HDL. In contrast, individuals with deficiencies in CETP activity due to mutations in the CETP gene have markedly elevated HDL levels.

The immune systems of higher organisms developed as a means for protecting the individual against invasion by deleterious foreign materials such as viruses, bacteria and parasites. Cells of the immune system are able to distinguish between materials from the individuals own body (termed "self" materials) and foreign material, or antigens. When foreign material enters the body, the immune system mounts a response. Antibodies that specifically recognize and bind to the foreign material are produced (the antibody or humoral response.) In addition, T cells are mobilized to repel the foreign substance (the T cell or cellular response.) Materials which are recognized as self do not normally stimulate such responses except in certain pathological conditions, primarily auto-immune disease. Even where the presence of an endogenous protein is itself deleterious, the immune system cannot serve as a regulator if the material is recognized as self.

Because of HDL'S potentially beneficial effect in preventing atherosclerosis, there exists a need for methods which can be used to increase its level in the serum. Such methods should ideally be specific and reliable and involve as little invasion of the body as possible. The present invention satisfies this need and provides related advantages as well.

SUMMARY OF THE INVENTION

The present invention provides a method for increasing HDL cholesterol in a mammal by stimulating an immune response that inhibits the function of CETP. Such an immune response can be induced by immunizing with CETP or fragments of CETP (together termed "CETP Peptides") which contain an epitope capable of stimulating such a response. The peptides can be conjugated to a carrier, such as Keyhole Limpet Hemocyanin (KLH) or ovalbumin, in order to increase immunogenicity. Adjuvants can also be administered.

In one embodiment, the fragments of CETP used to raise the antibody response are about ten to twenty amino acids in length and contain sequences homologous to the sequence in rabbit or human CETP.

DETAILED DESCRIPTION OF THE INVENTION

The present invention provides a means to utilize the body's own immune system to lower CETP levels, thereby increasing the level of beneficial HDL cholesterol. The invention provides an effective method of raising HDL in the blood or more specifically, the serum. By utilizing the body's own immune system to increase HDL levels, the invention avoids the problems associated with the repeated administration of drugs, which have undesirable side effects.

According to the present invention, CETP peptide is administered to an appropriate individual in such a manner as to elicit an anti-CETP immune response. The CETP can be chosen to contain an epitope capable of stimulating an antibody or humoral response. Alternatively, the CETP can stimulate a cellular response, or other immune response. CETP peptides can be elected to contain B cell epitopes, sequences capable of stimulating the production of antibodies that specifically recognize and bind to the epitope. Alternatively, CETP peptides can be chosen which stimulate a T cell or more general immune response.

Individuals exhibiting, or at risk of exhibiting, low serum levels of HDL cholesterol are particularly appropriate for such treatment. Serum HDL levels can be determined using methods well-known in the art (See Warnick, G. R. *J. Lipid. Res.*, 19:65 (1978), for example, which is incorporated herein by reference). Serum HDL of less than about 30–35 mg/dl is considered low. Subjects exhibiting a serum HDL level below this level are particularly suitable for the treatment of the invention.

The protein or peptide to be administered can be all or part of the CETP protein, so long as the protein or peptide contains a B cell and/or T cell epitope. As used herein, "CETP peptide" is intended to include both the full length CETP amino acid sequence as well as fragments thereof. The peptides can have a sequence corresponding to or homologous to a mammalian CETP sequence. It will be appreciated that the peptide can differ from the native sequence to some extent so long as it is capable of inducing antibodies that inhibit the activity of CETP.

CETP is a 55 kD protein based on its amino acid sequence, but with post-translational modifications it has an apparent molecular weight of 66–74 kD. The human CETP mRNA sequence is available in Genbank (accession number M30185). The rabbit CETP mRNA sequence is available in Genbank (accession number M27486). The genbank sequences were translated using the MacVector software program (I.B.M., New Haven, Conn.) to obtain the complete amino acids sequence of human and rabbit CETP.

Because CETP and its peptide derivatives may be recognized are "self" antigens, carriers can be used to increase their immunogenicity. Such carriers are well known in the art and include, for example, such compounds as Keyhole Limpet Hemocyanin (KLH), ovalbumin and Diphtheria toxoid (Wako BioProducts). The CETP peptides can be conjugated to such carriers by methods well-known in the art. See *Current Protocols in Molecular Biology*, Ausebell, Brent, Kingston, Moore, Seidman, Smith & Strull eds. (1987), or manufacturers' instructions, which is incorporated herein by reference. The immunogenicity of the peptides can be also increased by administration of a adjuvant. Various adjuvants are well-known and available. See *Antibodies: A Laboratory Manual*, Harlow and Lane eds., (1988) which is incorporated herein by reference.

The extent of the anti-CETP response induced by the administration of the CETP peptides can be monitored using a variety of assays. For example, competitive format immunoassays can be employed using anti-CETP antibodies or anti-CETP antiserum. Alternatively, the activity level of the CETP in the subject individual can be monitored using, for example a $^3$H-cholesterol oleate transfer assay. Lasuncion, M. A., et al. *Biochem J.*, 270:441–449 (1990). Reduction in CETP activity is an indirect indication of the anti-CETP response.

The following examples are intended to illustrate but not limit the invention.

EXAMPLE 1

Administration of CETP Peptide Immunogen

Peptides corresponding to portions of the human, rabbit and rabbit/human CETP were prepared according to standard peptide synthesis protocols. The following peptide sequences were prepared: H-Cys-Asp-Ser-Gly-Arg-Val-Arg-Thr-Asp-Ala-Pro-Asp-OH (SEQ ID No.: 1) H-Cys-Asp-Ala-Gly-Ser-Val-Arg-Thr-Asn-Ala-Pro-Asp-OH (SEQ ID No.: 2) H-His-Leu-Leu-Val-Asp-Phe-Leu-Gln-Ser-Leu-Ser-OH. (SEQ ID No.: 3)

The first peptide (SEQ ID 1) is taken from the Human CETP peptide sequence (residues 131–142 without signal peptide) from Smith and Barakat, *Med. Sci. Res.*, 21:911–912 (1993), which is incorporated herein by reference. The second peptide (SEQ ID 2) is the corresponding rabbit sequence and differs by only 3 amino acids from the human.

The third peptide (SEQ ID 3) is common to both human and rabbit and is an epitope recognized by anti-CETP-monoclonal antibody which is neutralizing. Tall, A. R., *J. Lipids Res.*, 34:1255–1257 (1993).

The peptides were conjugated to ovalbumin by the procedure of *Current Protocols in Molecular Biology*, supra. Of four New Zealand White rabbits, approximately four months of age, two were injected intramuscularly with 100 micrograms of the ovalbumin-conjugated human peptide (Seq. ID No.: 1) and CFA in PBS saline and two were injected with the equivalent human/rabbit peptide (Seq. ID No. 3). The animals were boosted twice at one month intervals with with the same peptides in IFA.

Although the invention has been described with reference to the presently preferred embodiments, it should be understood that various modifications can be made withouth departing from the spirit of the invention. Accordingly, the invention is limited only by the following claims.

What is claimed is:

1. A method of inducing an immune response that increases HDL cholesterol levels in a mammal exhibiting or at risk of exhibiting low levels of serum HDL cholesterol comprising administering to said mammal an immunogenic composition comprising a full-length cholesteryl ester transfer protein (CETP) and further comprising a carrier linked to said protein and wherein said immunogenic composition is capable of raising antibodies that recognize said mammal's endogenous CETP.

2. The method of claim 1, wherein said carrier is selected from the group consisting of keyhole limpet hemocyanin (KLH), ovalbumin, and Diptheria toxoid.

3. The method of claim 1 or 2, wherein said composition is administered with an adjuvant.

4. The method of claim 1, wherein said administration is repeated.

5. The method of 1, wherein said full-length CETP is the native CETP of said mammal.

6. The method of claim 1, wherein said full-length CETP is a human CETP.

7. The method of claim 1, wherein said full-length CETP is a rabbit CETP.

8. The method of claim 1, wherein said full-length CETP differs from the native CETP of said mammal.

* * * * *

SEQUENCE LISTING

```
<160> NUMBER OF SEQ ID NOS: 3

<210> SEQ ID NO 1
<211> LENGTH: 12
<212> TYPE: PRT
<213> ORGANISM: Homo sapiens

<400> SEQUENCE: 1

Cys Asp Ser Gly Arg Val Arg Thr Asp Ala Pro Asp
1               5                   10

<210> SEQ ID NO 2
<211> LENGTH: 12
<212> TYPE: PRT
<213> ORGANISM: Oryctolagus cuniculus

<400> SEQUENCE: 2

Cys Asp Ala Gly Ser Val Arg Thr Asn Ala Pro Asp
1               5                   10

<210> SEQ ID NO 3
<211> LENGTH: 11
<212> TYPE: PRT
<213> ORGANISM: Homo sapiens

<400> SEQUENCE: 3

His Leu Leu Val Asp Phe Leu Gln Ser Leu Ser
1               5                   10
```